United States Patent
Gome

(10) Patent No.: US 10,419,412 B1
(45) Date of Patent: Sep. 17, 2019

(54) INTEGRATING PATIENT PORTAL ACCESS INTO EHR GRAPHICAL USER INTERFACES

(71) Applicant: Allscripts Software, LLC, Raleigh, NC (US)

(72) Inventor: Ziv Gome, Kibutz Devira (IL)

(73) Assignee: ALLSCRIPTS SOFTWARE, LLC, Raleigh, NC (US)

(*) Notice: Subject to any disclaimer, the term of this patent is extended or adjusted under 35 U.S.C. 154(b) by 303 days.

(21) Appl. No.: 15/407,942

(22) Filed: Jan. 17, 2017

(51) Int. Cl.
| | |
|---|---|
| *H04L 29/06* | (2006.01) |
| *H04L 29/08* | (2006.01) |
| *H04L 12/24* | (2006.01) |
| *G16H 10/60* | (2018.01) |
| *G06F 3/0482* | (2013.01) |

(52) U.S. Cl.
CPC ............ *H04L 63/08* (2013.01); *G16H 10/60* (2018.01); *H04L 41/22* (2013.01); *H04L 63/10* (2013.01); *H04L 67/12* (2013.01); *G06F 3/0482* (2013.01)

(58) Field of Classification Search
CPC ..................................................... G16H 10/60
USPC ............................................................ 726/4
See application file for complete search history.

(56) References Cited

U.S. PATENT DOCUMENTS

| | | | |
|---|---|---|---|
| 9,208,284 B1 | 12/2015 | Douglass | |
| 9,959,385 B2* | 5/2018 | Liberty | .................. G06Q 50/24 |
| 2007/0198296 A1 | 8/2007 | Pellinat et al. | |
| 2009/0171696 A1 | 7/2009 | Allard et al. | |
| 2013/0218597 A1 | 8/2013 | Lorsch et al. | |
| 2016/0055300 A1* | 2/2016 | Ganesh | .................. G16H 10/60 705/3 |
| 2016/0063204 A1 | 3/2016 | Srinivasan | |
| 2016/0147946 A1* | 5/2016 | Von Reden | ............ G16H 10/60 705/3 |
| 2016/0210427 A1* | 7/2016 | Mynhier | ................. G06F 19/00 |
| 2016/0378297 A1* | 12/2016 | Velan | .................. G06F 3/04817 715/783 |
| 2017/0220782 A1* | 8/2017 | Alsanousi | ............. G06F 21/126 |
| 2018/0090231 A1* | 3/2018 | Liederman | ............ G06F 19/325 |
| 2018/0181712 A1* | 6/2018 | Ensey | ..................... H04L 67/10 |
| 2018/0181716 A1* | 6/2018 | Mander | .................. G16H 40/20 |
| 2018/0181720 A1* | 6/2018 | Ensey | ................. G06F 19/3418 |

* cited by examiner

*Primary Examiner* — Khalil Naghdali

(74) *Attorney, Agent, or Firm* — Medley, Behrens & Lewis, LLC

(57) ABSTRACT

Described herein are various technologies pertaining to a patient portal interface application for a hub application that is displayed concurrently on a display with a graphical user interface (GUI) for a client electronic health record application (EHR). The hub application facilitates access to supplement applications, wherein at least one of the supplement applications is a patient portal interface application. The patient portal interface application communicates with a patient portal server to facilitate presentment of patient portal data to a user of the client EHR. The patient portal interface application provides a current context of the EHR to the patient portal server, and receives contextually-based patient portal data from the patient portal server. The contextual patient portal data is then displayed by way of a GUI of the patient portal interface application.

20 Claims, 6 Drawing Sheets

INTEGRATING PATIENT PORTAL ACCESS INTO EHR GRAPHICAL USER INTERFACES

BACKGROUND

Electronic health record applications (EHRs) are robust applications that are utilized in medical facilities across a variety of aspects of a medical practice. For example, and not by way of limitation, an EHR can include functionality related to patient intake, billing, updating medical records, prescribing medication, tracking care over time, and so forth. Computer-executable applications have been developed to supplement EHRs, wherein such supplement applications cannot be considered EHRs themselves (e.g., the supplement applications do not provide the breadth of features of EHRs, fail to meet regulatory requirements imposed on EHRs by governmental bodies, etc.). A supplement application can, for example, provide data about a patient that supplements the data about the patient in the EHR.

Patient portals have also been developed to facilitate remote interaction and exchange of information between clinicians and patients. A patient portal can be accessed by a patient remotely by way of a computing device such as, for example, a home PC, smartphone, tablet computer, or the like. In order for a healthcare provider to access patient portal data, conventionally the healthcare provider must interrupt a workflow of an EHR application to launch a separate patient portal client application, thus losing a context of the EHR that may be relevant to the healthcare provider's needs in operating the patient portal client.

SUMMARY

The following is a brief summary of subject matter that is described in greater detail herein. This summary is not intended to be limiting as to the scope of the claims.

Described herein are various technologies pertaining to computer-executable applications that are well-suited for use in a healthcare environment. More specifically, described herein are various technologies pertaining to a computer-executable supplement application that can be utilized simultaneously with an EHR, where the supplement application is configured to provide a healthcare worker that uses the EHR with contextually relevant information about a patient and/or population of patients.

In an exemplary embodiment, a client computing device can execute both a client EHR and a hub application. The hub application is configured to provide a unified graphical user interface by way of which a plurality of supplement applications can be accessed, and further by way of which information output by the plurality of supplement applications can be presented. The hub application is configured to receive data from the client EHR; thus, for instance, when the client EHR has information about a patient and/or clinician loaded therein, the client EHR can transmit an identifier for the patient and/or an identifier for the clinician to the hub application. A graphical user interface (GUI) of the hub application can include a header field, wherein information about the patient and/or clinician is displayed in the header field. For instance, the header field can display the patient name, demographic information about the patient, a patient identifier (such as a medical record number), and so forth. Such information can be received, for instance, from the client EHR. Additionally, the GUI of the hub application can include an applications ribbon, wherein a plurality of selectable buttons that correspond to a respective plurality of supplement applications are displayed. When a button in the plurality of selectable buttons is selected, the hub application causes a GUI for a supplement application that corresponds to the selected button to be presented on the display. Thus, when the supplement application is being executed in the background, selection of the button causes the supplement application to be executed in the foreground. When the supplement application is not being executed, selection of the button causes the supplement application to be executed.

At least one of the supplement applications can be a patient portal interface application. The patient portal interface application is configured to communicate with a patient portal server. The patient portal server also communicates with patient portal clients operated by patients in connection with viewing and providing health data for the patients. The patient portal interface application receives a current context of the client EHR from the hub application and transmits the context to the patient portal server. The patient portal server receives the context and provides patient portal data to the patient portal interface application based upon the context. The patient portal interface application displays the patient portal data received from the patient portal server in a GUI that can be displayed concurrently with a GUI of the client EHR. In contrast to conventional patient portal interface systems, the patient portal interface application can display data relating to a patient portal without interrupting an EHR workflow of an end user of the EHR, and without losing an EHR context that may be relevant to the end user's operation of the patient portal interface.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
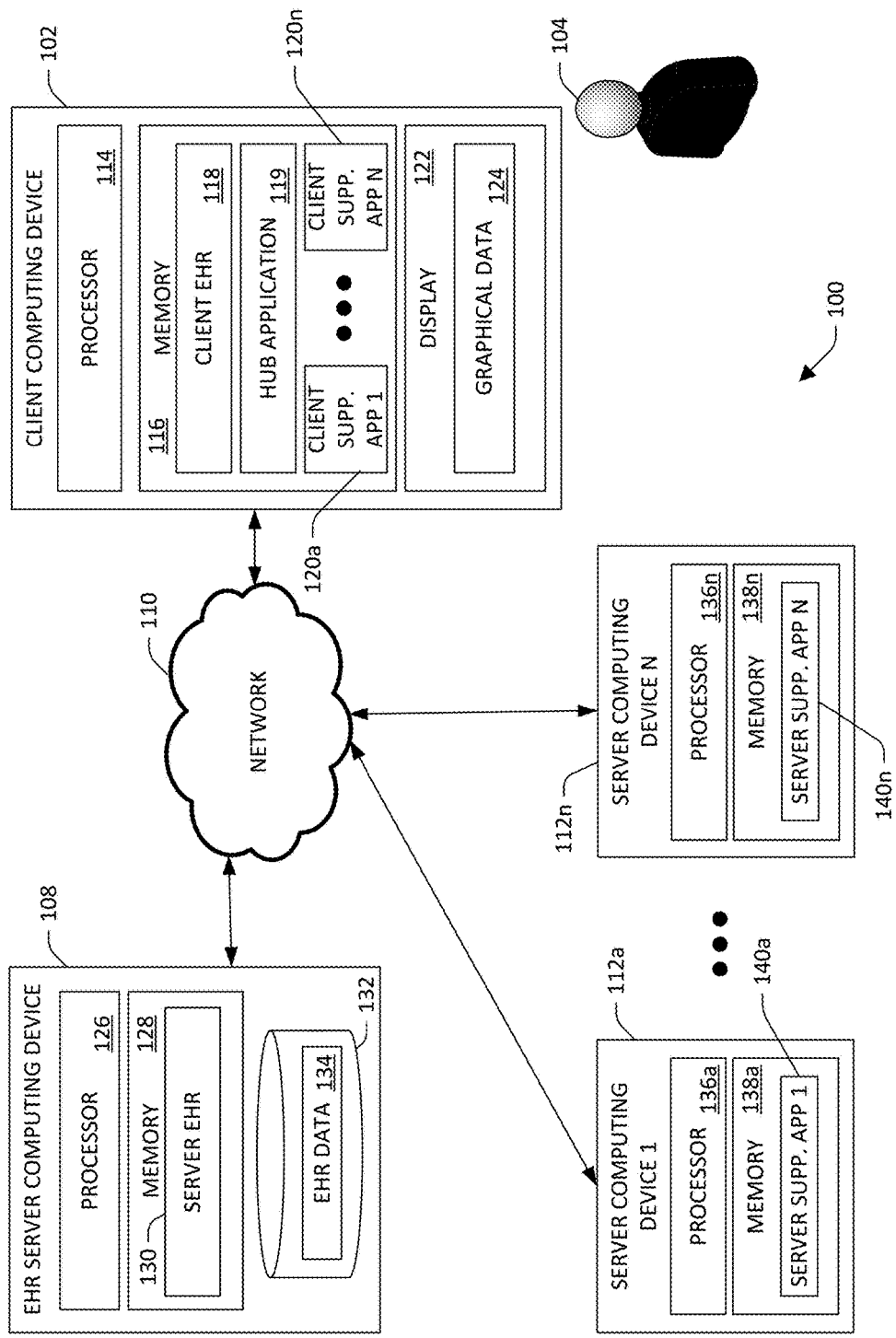
FIG. 1 is a functional block diagram of an exemplary system that facilitates presentment of supplemental data to a user of an EHR.

Various technologies pertaining to supplement applications that are configured to present contextually relevant data to a healthcare worker are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, the features described herein pertain to technologies for displaying graphical data to a clinician that is relevant to a current context of the clinician. More specifically, a clinician can employ an electronic health record application (EHR), wherein the EHR is a distributed application that includes a client-side application (client EHR) executing on a client computing device and a server-side application (server EHR) executing on a server computing device, and further wherein the client EHR and the server EHR are in communication with one another. For instance, the client EHR can receive authentication data from a clinician, and can further receive data that is indicative of an identity of a patient. The client EHR can transmit such data to the server EHR, which can authenticate the clinician and acquire information about the patient from a database (where the clinician is authorized to view the information). The server EHR can transmit this information to the client EHR, wherein the client EHR presents such information to the clinician.

The client computing device can further execute a hub application that is in communication with the client EHR. The hub application is configured to provide a graphical user interface (GUI), wherein the GUI of the hub application presents information that is relevant to the current context of the client EHR. Thus, in an example, the hub application can present data that is relevant to a patient whose record is being presented to the clinician by way of the client EHR. The GUI of the hub interface also includes a ribbon, wherein the ribbon comprises a plurality of buttons, and further wherein each button corresponds to a respective supplement application.

A supplement application is one that is in communication with the client EHR, and is configured to present data to an end user (e.g., a clinician) that supplements what is being displayed to the end user by way of the client EHR. Hence, for example, if the client EHR is presenting information about a patient to a clinician (e.g., such as a patient record), the client EHR can provide the supplement application with data that is indicative of an identity of the patient. The supplement application may then be configured to retrieve population data that is relevant to the patient, wherein such data can be presented to the clinician by way of the supplement application (e.g., simultaneously with data that is presented to the end user by way of the client EHR). Additionally, similarly to the EHR, a supplement application is a distributed application that includes a client supplement application (executed on the client computing device) and a server supplement application (executed on a server computing device). The client supplement application is configured to present data to an end user and receive input from the end user, while the server supplement application is configured to perform backend processing based upon data received by the client supplement application from the client EHR.

The supplement application can be a patient portal interface application that is configured to present or receive data pertaining to a patient portal based upon current context of the client EHR such as an identity of the end user or an identity of a patient in view in the client EHR. The patient portal interface application receives the context of the client EHR from the hub application. The patient portal interface application provides the context to a patient portal server that in turn transmits patient portal data to the patient portal interface application based upon the context. In contrast to conventional approaches, the patient portal interface application can display data relating to a patient portal without interrupting an EHR workflow of an end user of the EHR (e.g., without requiring the end user to minimize the EHR application and open a separate patient portal application). In further contrast to conventional approaches, the patient portal interface application can operate concurrently with a variety of different EHRs and a variety of different patient portals, wherein the EHRs and patient portals may not be configured to communicate or integrate functionality.

Now referring to FIG. 1, an exemplary system 100 that facilitates presenting contextually-relevant supplemental data simultaneously with data presented by way of a client EHR is illustrated. The system 100 includes a client computing device 102 that is operated by a healthcare worker 104 (e.g., a clinician, a billing specialist, etc.). The healthcare worker 104 may be utilizing the client computing device 102 in connection with providing care to a patient (not shown). The patient may be in close proximity to the healthcare worker 104, or the healthcare worker may be providing care to the patient remotely. The client computing device 102 operated by the healthcare worker 104 may be any suitable type of client computing device, including a desktop computing device, a laptop computing device, a mobile telephone, a tablet computing device, a wearable computing device, or the like.

The system 100 further includes an EHR server computing device 108 that is in communication with the client computing device 102 by way of a suitable network 110, such as the Internet, an intranet, or the like. The system 100 additionally includes a plurality of server computing devices 112a-112n that are in communication with the client computing device 102 by way of the network 110. While the system 100 is illustrated as including numerous server computing devices, it is to be understood that actions undertaken by several server computing devices may be performed by a single server computing device. Further, actions described as being performed by a single server computing device may be performed by multiple server computing devices. Moreover, while the client computing device 102 is depicted as being in communication with the server computing devices 108 and 112a-112n by way of the network 110, it is to be understood that the client computing device 102 may be in communication with the server computing devices 108 and 112a-112n over different networks. Further, the EHR server computing device 108 can be an enterprise device, whose operation is controlled by a healthcare enterprise. In another example, the EHR server computing device 108 can be a cloud-based computing device, where maintenance and operation of the EHR server computing device 108 is handled by a company that provides an EHR for use by a healthcare enterprise. Typically, the server computing devices 112a-112n are cloud-based computing devices, where maintenance and operation of the server computing devices 112a-112n is under the control of entities that are separate from the healthcare enterprise.

The client computing device 102 includes a processor 114 and memory 116. The memory 116 stores instructions that are executed by the processor 114. More specifically, the memory 116 includes a client EHR 118, a hub application 119, and a plurality of client supplement applications 120a-120n. As will be described in greater detail herein, each client supplement application in the client supplement applications 120a-120n is configured to acquire data that is contextually relevant to information being presented to the healthcare worker 104 by way of the client EHR 118, and is further configured to present the contextually relevant data upon request. The client computing device 102 further comprises a display 122, which is configured to present graphical data 124 to the healthcare worker 104. The graphical data 124 may include data presented by way of the client EHR 118, a GUI of the hub application 119, and data presented by way of one or more of the client supplement applications 120a-120n. While the display 122 is depicted as being integral to the client computing device 102, it is to be understood that the display 122 may be externally coupled to the client computing device 102 or may be a projected display.

The EHR server computing device 108 comprises a processor 126 and memory 128 that stores instructions that are executed by the processor 126. As shown in FIG. 1, the memory 128 includes a server EHR 130. The EHR server computing device 108 further includes a data store 132 that comprises EHR data 134. In operation, the healthcare worker 104 can interact with the client EHR 118 executing on the client computing device 102. This interaction causes the client EHR 118 to transmit data to the server EHR 130 executing on the EHR server computing device 108. Content of the data transmitted to the server EHR 130 can include, for instance, data that identifies the healthcare worker 104 and data that identifies the patient 106, amongst other data. Responsive to receipt of such data, the server EHR 130 can construct a query based upon the data and search over the EHR data 134 in the data store 132 based upon the query, thereby obtaining search results. The EHR data 134 can include any suitable data that is used in connection with provision of care to the patient 106, including an electronic patient record for the patient 106. The server EHR 130 then causes the EHR server computing device 108 to transmit the search results to the client computing device 102, whereupon the search results are provided to the client EHR 118. The client EHR 118 subsequently causes at least a portion of the search results to be presented in the graphical data 124 on the display 122 of the client computing device 102.

In a more specific example, the healthcare worker 104, through utilization of a human machine interface (HMI), can interact with the client EHR 118 by providing input pertaining to the patient (referenced above). The client EHR 118 transmits this information to the server EHR 130, which can construct a query based upon the data and search over the EHR data 134 using the query. The server EHR 130 can then return corresponding search results to the client EHR 118. The client EHR 118 causes at least a portion of the search results (e.g., a portion of an electronic medical record (EMR) of the patient) to be displayed on the display 122 (e.g., as part of the graphical data 124).

The server computing devices 112a-n include respective processors 136a-n and respective memory 138a-n, wherein the memory 138a-n store instructions that are executed by the processors 136a-n. As shown, the memory 138a-n include respective server supplement applications 140a-n, wherein the server supplement applications 140a-n respectively correspond to the client supplement applications 120a-n. At least one of the server supplement applications 140a-n can be configured to search over population data in a data store (not shown), where the population data can be acquired from several different data sources. For instance, the data sources may include another EHR application, web pages, a healthcare information exchange (HIE), etc. It can therefore be ascertained that the population data can include population health data retrieved and aggregated from a myriad of different data sources, wherein at least some of the population data pertains to the patient and is not duplicative as to data about the patient in the EHR data 134.

Operation of the hub application 119, the client supplement applications 120a-120n, and the server supplement applications 140a-140n is now described. The hub application 119 operates as a platform for the supplement applications 120-120n, such that the supplement applications 120-120n can be launched by way of the hub application 119, and further wherein the hub application 119 can present data that indicates that the supplement applications 120a-120n have produced one or more events related to the current context of the client EHR 118. Further, in an exemplary embodiment, the hub application 119 can communicate with the server supplement applications 140a-n directly. In another exemplary embodiment, the hub application 119 can communicate with the server supplement applications 140a-n indirectly (e.g., by way of the client supplement applications 120a-120).

The client EHR 118 is operated by the healthcare worker 104, such that the context of the client EHR 118 changes. For instance, the client EHR 118 can receive input from the healthcare worker 104 pertaining to a particular patient, and the client EHR 118 can direct such input to the server EHR 130. The server EHR 130 can execute a query over the EHR data 134 based upon the input received from the client EHR 118, and can direct the search results to the client EHR 118. These search results can include data that identifies the patient, demographics about the patient, and the like. The client EHR 118 can cause at least a portion of the search results to be presented on the display 122 of the client computing device 102; thus, the context of the client EHR 118 has changed.

As indicated above, the client EHR 118 is in communication with the hub application 119, and is further optionally in communication with client supplement applications 120a-n. In an exemplary embodiment, the client EHR 118 can transmit data that is indicative of the current context of the client EHR 118 to the hub application 119. Responsive to receiving the data that is indicative of the current context of the client EHR 118, the hub application 119 can update the GUI of the hub application 119 to depict, for instance, the name of the patient whose information is presented by way of the client EHR 118, demographic information about the patient (e.g., age, gender, geographic location), and so forth.

Further, the client supplement applications 120a-120n can receive the data that is indicative of the current context of the client EHR 118. In an example, the hub application 119 can provide the client supplement applications 120a-120n with the data that is indicative of the current context of the client EHR 118 in response to receipt of such data from the client EHR 118. In another example, the client supplement applications 120a-120n can be configured to receive the data that is indicative of the context of the client EHR 118 directly from the client EHR 118.

The client supplement applications 120a-120n, in response to receiving the data that is indicative of the current context of the client EHR 118, can transmit such data to their respective server supplement applications 140a-140n. A server supplement application, upon receipt of this data, performs a computing operation in accordance with the intended function of the server supplement application. For instance, a client supplement application can be a patient portal interface application and a server supplement application can be a patient portal server application. The patient portal interface application can receive data indicative of the current context of the client EHR 118, such as an identity of a patient whose EHR patient data is being viewed in the client EHR 118. The patient portal interface application can transmit the data to the patient portal server application, responsive to which the patient portal server application transmits patient portal data to the patient portal interface application, wherein the patient portal data is based upon the context. The patient portal interface application, or the hub application, can display the patient portal data simultaneously with an interface of the client EHR 118.

While FIG. 1 depicts a specific architecture for the system 100, and data has been described as being directed from the client EHR 118 to the hub application 119, from the hub application 119 to the client supplement applications 120a-120n, from the client supplement applications 120a-120n to the server supplement applications 140a-140n, from the server supplement applications 140a-140n back to the client supplement applications 120a-120n, and from the client supplement applications 120a-120n to the hub application, other architectures and data flows are also contemplated. For example, the hub application 119 may be a distributed application, such that it has a server-side component. In an exemplary embodiment, data can flow from the hub application 119 to its server-side counterpart, and from such counterpart to the server supplement applications 140a-140n. In another example, the hub application 119 may communicate directly with the server supplement applications 140a-140n, such that the hub application 119 acts as a broker between the client supplement applications 120a-120n and the server supplement applications 140a-140n. Other architectures and data flows are also contemplated.

Figure 2:
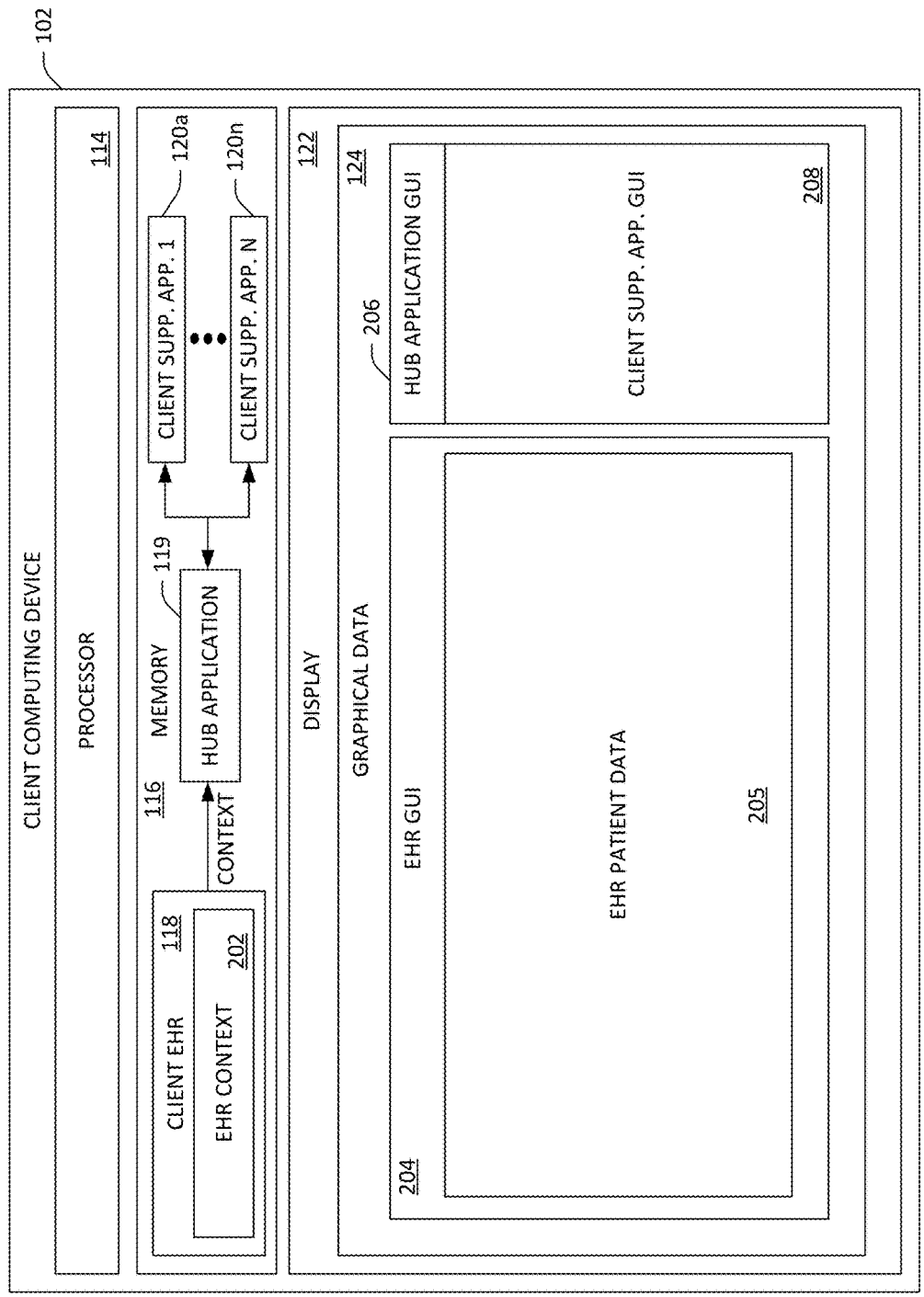
FIG. 2 depicts an exemplary client computing device.

With reference now to FIG. 2, a functional block diagram of the client computing device 102 is illustrated. As indicated previously, the client EHR 118 is loaded in the memory 116 and is executed by the processor 114. The client EHR 118 has an EHR context 202, where the EHR context 202 is indicative of a current state of the client EHR 118, which can include an identity of the healthcare worker 104 utilizing the client EHR 118, an identity of the patient (e.g., when data about the patient is loaded into the client EHR 118), etc. The processor 114, when executing the client EHR 118, causes a client EHR GUI 204 to be included in the graphical data 124 on the display 122. In this example, the client EHR GUI 204 comprises EHR patient data 205 (data about the patient). The client EHR 118 can provide the EHR context 202 to the hub application 119, which in turn can provide the EHR context 202 to the client supplement applications 120a-120n, as described above.

The processor 114, when executing the hub application 119, causes a hub application GUI 206 corresponding to the hub application 119 to be presented on the display 122 as a part of the graphical data 124. As will be described in greater detail below, the hub application GUI 206 can include several buttons, where the buttons are respectively representative of the supplement applications (the client supplement applications 120a-120n and the server supplement applications 140a-140n). When the healthcare worker 104 selects a button in the hub application GUI 206, the processor 114 can present a client supplement application GUI 208 for the supplement application represented by the selected button. The client supplement application GUI 208 can be presented to appear integrated with the hub application GUI 206.

Figure 3:
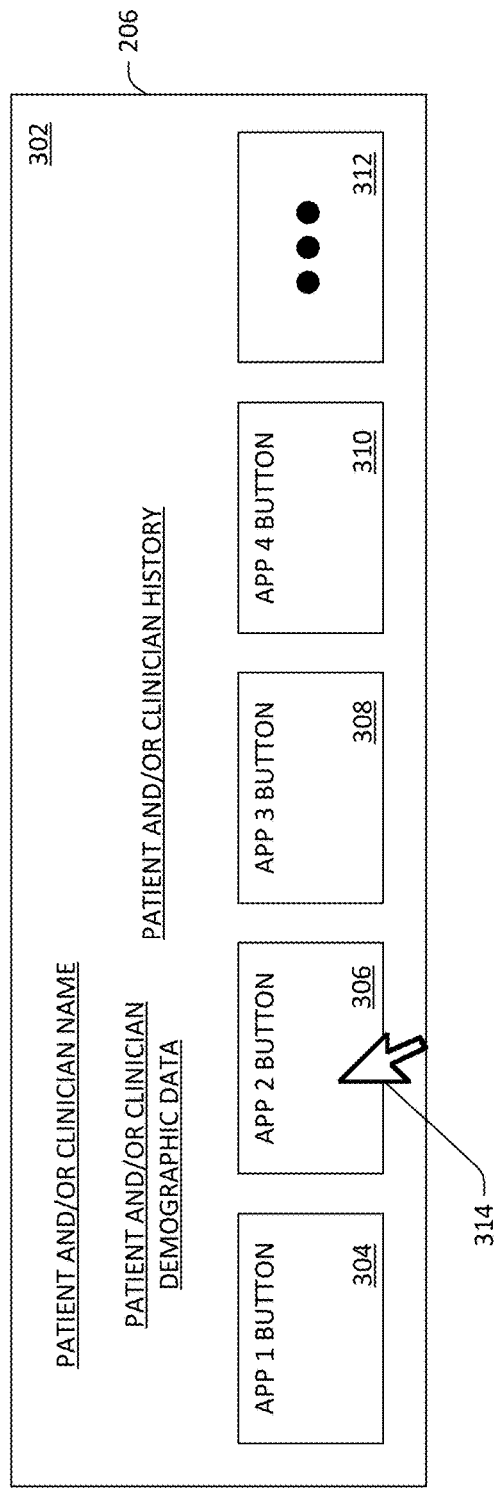
FIG. 3 depicts an exemplary hub application GUI.

With reference to FIG. 3, an exemplary illustration of the hub application GUI 206 is illustrated. In the example shown in FIG. 3, the hub application GUI 206 includes a ribbon 302. The ribbon 302 includes at least a portion of the EHR context 202. For instance, the ribbon 302 can include the name of the patient, the name of the healthcare worker 104, patient and/or clinician demographic data (date of birth, gender, etc.), and optionally, patient and/or clinician history (time of last encounter). The patient and/or clinician name can further include a unique identifier for the patient and/or clinician in the client EHR 118. The ribbon 302 may further include selectable application buttons 304-312 that respectively represent a plurality of supplement applications. Responsive to selection of one of the buttons 304-312, for example by way of a cursor 314, one of the plurality of supplement applications that corresponds to the selected button can be launched, or the supplement application can be brought to the foreground in the graphical data 124.

Figure 4:
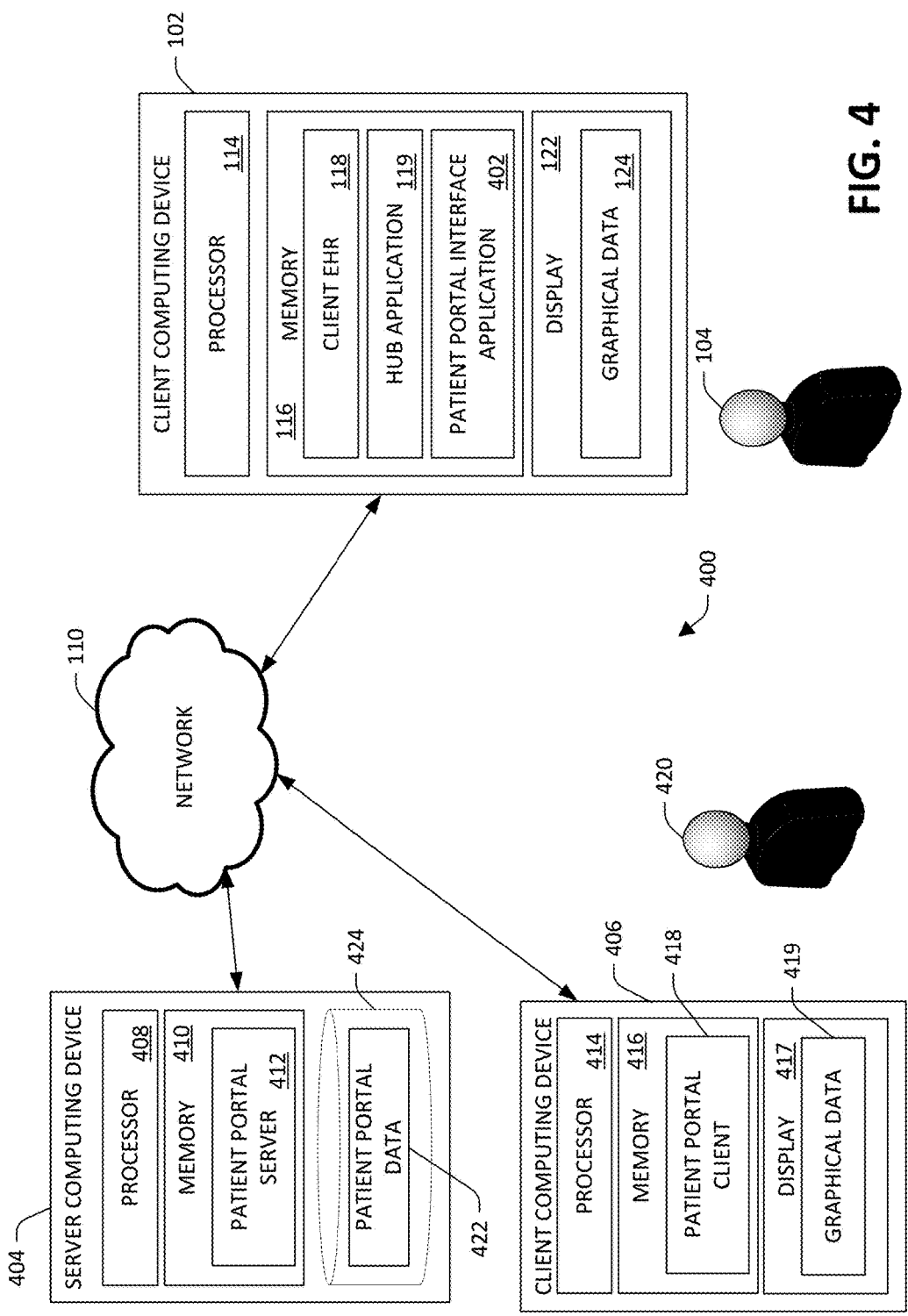
FIG. 4 is a functional block diagram of an exemplary system that facilitates presentment of supplemental data pertaining to a patient portal to a user of an EHR.

Referring now to FIG. 4, an exemplary system 400 that facilitates presentation of patient portal data concurrently with graphical user interfaces of an EHR is illustrated. The system 400 includes the client computing device 102, operated by the healthcare worker 104, and which executes a patient portal interface application 402. The system 400 further includes a server computing device 404 in communication with the client computing device 102 by way of the network 110, and a second client computing device 406 that is in communication with the server computing device 404. The server computing device 404 includes a processor 408 and memory 410 that includes a patient portal server application 412 executed by the processor 408. The second client computing device 406 includes a processor 414 and memory 416 that includes a patient portal client application 418 executed by the processor 414, as well as a display 417 on which is displayed graphical data 419.

The patient portal server application 412 and the patient portal client application 418 executing on the server computing device 404 and the client computing device 406, respectively, provide patient portal functionality that allows a patient-user 420 of the client computing device 406 to access his or her health data, communicate with healthcare providers, input self-reported patient health data, etc. For instance, the patient 420 can log into the patient portal client 418, whereupon the patient portal client 418 transmits the patient's credentials to the patient portal server 412. Responsive to receiving the credentials of the patient 420, the patient portal server 412 transmits data pertaining to the patient to the patient portal client 418. The data transmitted by the patient portal server 412 to the patient portal client 418 is patient portal data 422 that is stored at a data store 424 of the server computing device 404. The patient portal data 422 can be substantially any data pertaining to patients registered to the patient portal server 412, for example demographic data, patient health data, patient health goals set by clinicians, etc. Responsive to receiving patient portal data from the patient portal server 412, the patient portal client 418 can display the patient portal data as all or part of the graphical data 419 on the display 417. Furthermore, the patient portal client 418 can present one or more input fields on the display 417 by way of which the patient 420 can input patient-generated patient data. Upon receiving such input, the patient portal client 418 can transmit the patient-generated patient data to the patient portal server 412, whereupon the patient portal server 412 retains the patient-generated patient data as part of the patient portal data 422. It is further to be understood that the server computing device 404 that executes the patient portal server application 412 can receive EHR data pertaining to one or more patients from the EHR server computing device 108 (FIG. 1), and the patient portal data 422 can include such EHR data.

The client computing device 102 can execute the patient portal interface application 402 responsive to receiving a selection of the patient portal interface application 402 by way of the hub application 119 (e.g., detecting that a button corresponding to the patient portal interface application 402 has been selected). In an initial interaction with the patient portal interface application 402, the healthcare worker 104 can be prompted to provide user credentials with respect to the patient portal server application 412. In subsequent interactions with the patient portal interface application 402, the hub application 119 can provide the user credentials of the healthcare worker 104 to the patient portal interface application 402 with context data of the client EHR 118. For example, the user credentials can be retained by the client hub application 119 or can be retrieved by the hub application 119 from an affiliated application with which the healthcare worker 104 is already logged in, such as the server EHR 130 (FIG. 1). Thus, when a user of the client computing device 102 is logged into the server EHR 130 by way of the client EHR 118, the hub application 119 can provide credentials of the user to the patient portal interface application 402 responsive to selection of the application 402.

The patient portal interface application 402, responsive to receiving the EHR context from the hub application 119, transmits data indicative of the context to the patient portal server application 412 executing on the server computing device 404. For instance, the patient portal interface application 402 can transmit to the patient portal server 412 a clinician identifier that identifies the healthcare worker 104 or a patient identifier that identifies a patient whose data is currently in view in a GUI of the client EHR 118. Responsive to receiving the context data from the client computing device 102, the patient portal server 412 transmits first data to the patient portal interface application 402, wherein the first data is patient portal data that is based at least in part upon the context data. The first data can include at least a part of the patient portal data 422 that is stored by the server computing device 404 responsive to receiving patient data from the second client computing device 406. The patient portal server 412 can provide the first data based at least in part upon an authorization level of the healthcare worker 104 with respect to data of the patient 420. In an example, when inputting patient data by way of the patient portal client 418, the patient 420 can specify a level of authorized access with respect to the patient data, and the access level can be stored by the server computing device 404 with the patient portal data 422.

Some exemplary use cases of the patient portal interface application 402 in conjunction with the system 400 are now described. In a first use example, the healthcare worker 104 can operate the patient portal interface application 402 to subscribe or register a patient to the patient portal server application 412. For instance, when the healthcare worker accesses a health record of a patient by way of the client EHR 118, the client EHR 118 can present an indication on the display 122 of whether or not the patient is registered with the patient portal server 412. If the patient is not registered with the patient portal server 412, the healthcare worker 104 can select the patient portal interface application 402 by way of a GUI of the hub application 119. Responsive to receiving the selection, the client computing device 102 executes the patient portal interface application 402 and presents a GUI for the application 402 on the display 122. The GUI can be configured to receive input from the healthcare worker 104 relative to a process for registering a patient with the patient portal server 412. For instance, the GUI can prompt the healthcare worker 104 for input pertaining to the patient's name, contact information, login information, etc. Upon receiving the input from the healthcare worker 104, the patient portal interface application 402 transmits the input data to the patient portal server 412, wherein the data is configured to cause the patient portal server 412 to register the patient and to retain patient data in the patient portal data 422.

In a second use example, the patient portal interface application 402 can be used in connection with presenting a patient portal message inbox to the healthcare worker 104. The patient-user 420 of the second client computing device 406 can send messages to his or her clinician (e.g., the healthcare worker 104) by way of the patient portal client 418. The patient portal client 418 can receive a message input by the patient 420, and transmits the message to the patient portal server 412. The patient portal server 412 stores the message in the data store 424 as part of the patient portal data 422, wherein the message is associated with an identifier of the clinician of the patient 420. When the healthcare worker 104 opens the patient portal interface application, the application 402 transmits the current context of the client EHR 118 to the patient portal server 412, wherein the context includes an identifier of the healthcare worker 104. Responsive to receiving the context, the patient portal server 412 transmits data comprising the message to the patient portal interface application 402, whereupon the application 402 causes the message to be displayed as part of the graphical data 124. The patient portal interface application 402 can simultaneously display a plurality of messages received from the patient portal server 412. Further, the messages can be messages generated by a plurality of patients associated with the healthcare worker 104.

In a third exemplary use of the patient portal interface application 402, the healthcare worker 104 can view or modify a patient health goal (e.g., target weight, exercise goals, diet plans, etc.) that is tracked by the patient portal server application 412. The patient portal client 418 can display to the patient-user 420 of the second client computing device 406 data relating to a health goal. The health goal can be a goal set, for example, by a healthcare provider of the patient 420 who is authorized to access patient portal data for the patient 420. Patient health goal data can be retained by the patient portal server 412 in the patient portal data 422, and the health goal data can be accessed by the patient 420 by way of the patient portal client. Responsive to receiving context data that includes an identifier of the patient 420 from the patient portal interface application 402, the patient portal server 412 can transmit health goal data pertaining to the patient 420 to the patient portal interface application 402. The healthcare worker 104 can view the health goal data on the display 122. The healthcare worker 104 can modify the health goal by providing user input to the patient portal interface application 402, whereupon the application 402 can transmit data to the patient portal server 412 that is configured to update the health goal data for the patient 420.

Figure 5:
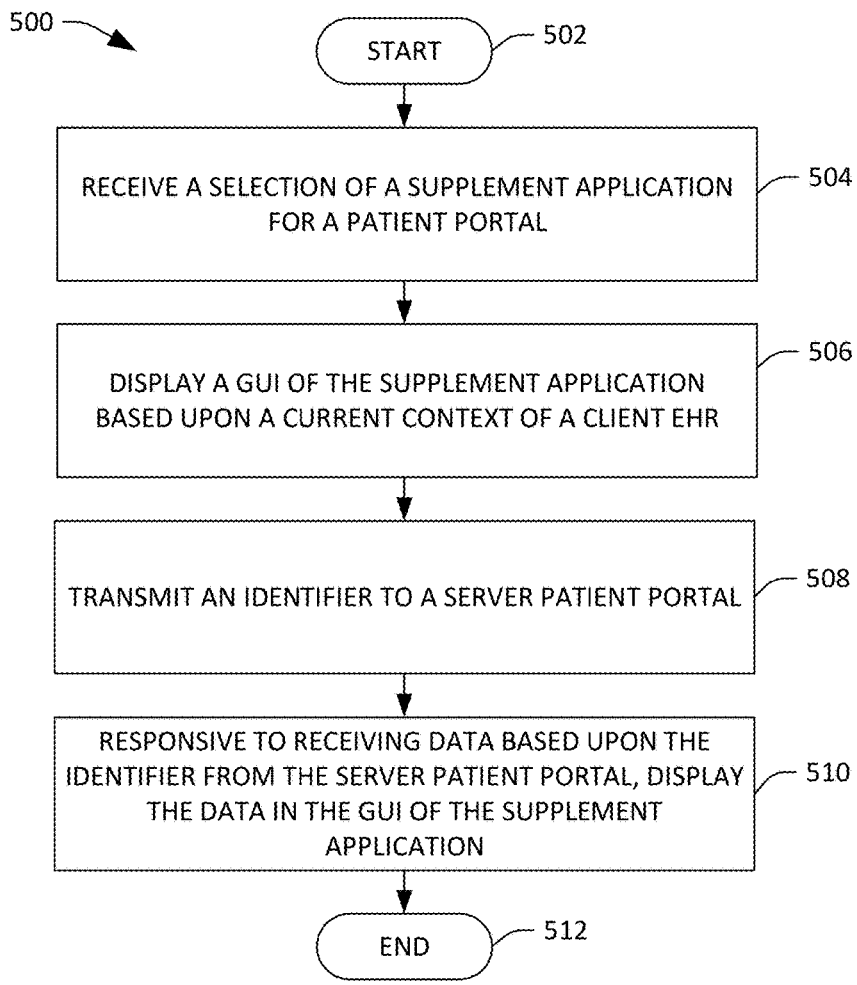
FIG. 5 is a flow diagram illustrating an exemplary methodology for providing supplemental patient portal data to a user of a client EHR.

FIG. 5 illustrates an exemplary methodology relating to presentment of contextually relevant patient portal content to a healthcare worker using an EHR. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 5, an exemplary methodology 500 for presenting patient portal data that is performed by a client computing device that executes a client EHR, a hub application, and a supplement application is illustrated. The methodology 500 starts at 502, and at 504, at the hub application, a selection of a supplement application for a patient portal is received. The supplement application is configured to exchange data with the hub application, which hub application can itself be configured to exchange data with the client EHR, wherein the client EHR may be one of a variety of EHR applications that the hub application can be configured to communicate with. At 506, responsive to receiving the selection of the patient portal supplement application at 504, a GUI of the patient portal supplement application is displayed based upon a current context of the client EHR. The patient portal supplement application receives the context by way of the hub application, wherein the context can include an identifier of a clinician user of the client computing device and/or an identifier of a patient in view in a GUI of the client EHR. At 508 an identifier is transmitted by the patient portal supplement application to a server patient portal application executing on a server computing device. The identifier can comprise the clinician identifier, the patient identifier, or both. At 510, responsive to receiving data based upon the identifier from the server patient portal application, the data is displayed in the GUI of the patient portal supplement application, wherein the GUI can be displayed concurrently with a GUI of the client EHR. The data can include substantially any data that can be accessed by way of a patient portal. Thus, the methodology 500 facilitates presentment of patient portal data to a clinician user of a client EHR, without interfering with the clinician's EHR workflow. The methodology 500 completes at 512.

Figure 6:
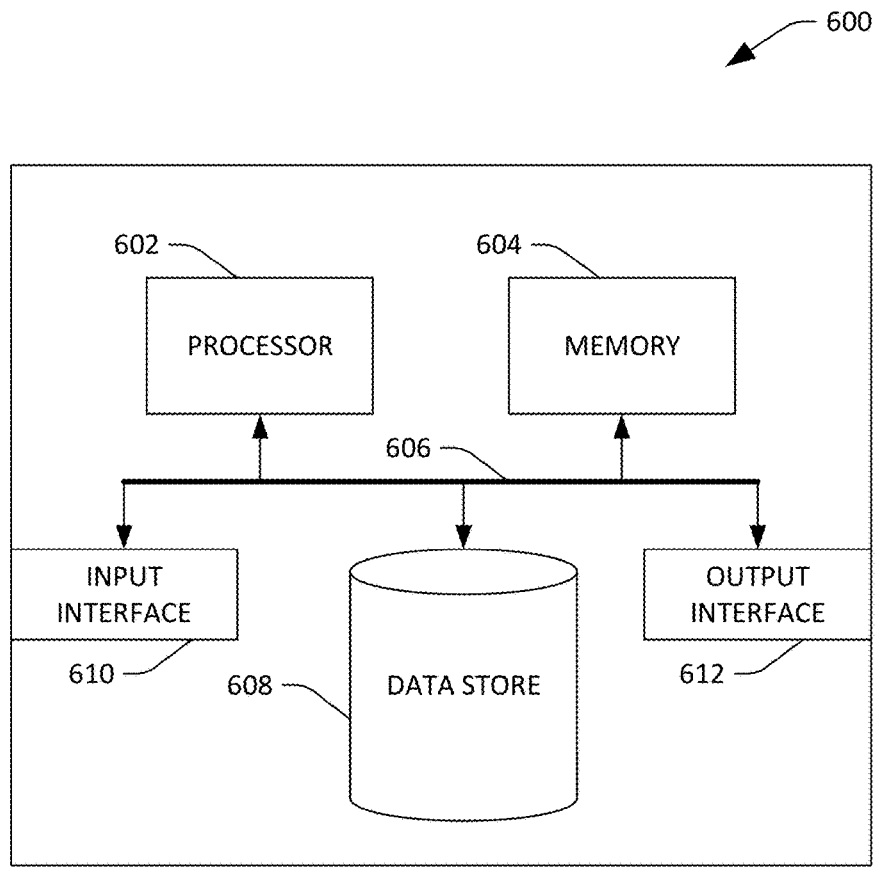
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that executes an EHR. By way of another example, the computing device 600 can be used in a system that executes a supplement application and/or hub application. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store patient-centric data, population data, patient portal data, etc.

The computing device 600 additionally includes a data store 608 that is accessible by the processor 602 by way of the system bus 606. The data store 608 may include executable instructions, patient-centric data, population data, patient portal data, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing device comprising:
at least one processor; and
memory comprising instructions that, when executed by the at least one processor, cause the at least one processor to perform acts comprising:
responsive to receiving a selection of a supplement application that pertains to a patient portal, the selection received by way of a graphical user interface (GUI) of a hub application, displaying a GUI of the supplement application, the GUI of the supplement application based upon current context of a client electronic health record application (EHR) being executed by the at least one processor;
transmitting an identifier to a server patient portal application executing on a second computing device, the identifier based upon the context; and
responsive to receiving first data from the server patient portal application executing on the second computing device, the first data based upon the identifier, displaying the first data in the GUI of the supplement application.

2. The computing device of claim 1, wherein the identifier comprises an identity of a patient, the first data being data pertaining to the patient.

3. The computing device of claim 2, wherein the first data is data generated by the patient by way of a patient portal client.

4. The computing device of claim 3, the identifier further comprising an identity of a user of the computing device, the first data based upon an authorization level of the user with respect to the patient.

5. The computing device of claim 1, wherein the identifier comprises an identity of a user of the computing device.

6. The computing device of claim 5, wherein the first data comprises a message inbox for the user of the computing device, the message inbox associated with the patient portal application.

7. The computing device of claim 1, the acts further comprising:
receiving patient data pertaining to a patient that is input by a user of the computing device by way of the GUI of the supplemental application; and
transmitting the patient data to the second computing device, wherein the patient data causes the second computing device to update patient portal data retained at the second computing device responsive to the patient data being received at the second computing device.

8. The computing device of claim 7, wherein the patient data causes the second computing device to subscribe the patient to the patient portal responsive to the patient data being received at the second computing device.

9. The computing device of claim 7, wherein the patient data causes the second computing device to update health goal data for the patient responsive to the patient data being received at the second computing device, the health goal data retained at the second computing device.

10. A computer-executable method, comprising:
responsive to receiving a selection of a supplement application pertaining to a patient portal by way of a hub application, displaying a graphical user interface (GUI) of the supplement application, the GUI of the supplement application based upon a current context of a client electronic health record application (EHR);
transmitting context data to a server patient portal application executing on a server computing device, the context data based upon the current context of the client EHR; and
responsive to receiving first data from the server patient portal application, the first data based upon the context, displaying the first data in the GUI of the supplement application.

11. The computer-executable method of claim 10, wherein the first data is displayed in the GUI of the supplement application concurrently with a GUI of the client EHR.

12. The computer-executable method of claim 10, wherein the context data comprises an identifier of a clinician user of the client EHR.

13. The computer-executable method of claim 12, wherein the first data comprises a message inbox for the clinician user, the message inbox associated with the server patient portal application.

14. The computer-executable method of claim 13, wherein the message inbox comprises a plurality of messages, the messages being messages input by a patient by way of a patient portal client application.

15. The computer-executable method of claim 10, wherein the context data comprises an identifier of a patient, the first data being data pertaining to the patient.

16. The computer-executable method of claim 15, wherein the context data further comprises an identity of a clinician user of the client EHR, the first data based upon an authorization level of the clinician user with respect to the patient.

17. The computer-executable method of claim 10, further comprising:

responsive to receiving patient data by way of the GUI of the supplement application, transmitting the patient data to the server computing device, wherein the patient data causes the server computing device to update patient portal data retained at the server computing device responsive to the patient data being received at the server computing device.

18. The computer-executable method of claim 17, wherein the patient data causes the server computing device to register a patient with the server patient portal application responsive to the patient data being received at the server computing device.

19. The computer-executable method of claim 17, wherein the patient portal data comprises health goal data, and wherein the patient data causes the server computing device to update health goal data retained at the server computing device responsive to the server computing device receiving the patient portal data.

20. A computing device comprising:

at least one processor; and memory comprising instructions that, when executed by the at least one processor, cause the at least one processor to perform acts comprising:

responsive to receiving a selection of a patient portal interface application by way of a hub application being executed by the computing device, transmitting context data to a server computing device executing a patient portal server application, the context data based upon a current context of a client electronic health record application (EHR) being executed by the computing device; and responsive to receiving patient portal data from the server computing device, the patient portal data based upon the context data, displaying the patient portal data in a graphical user interface (GUI) of the patient portal interface application concurrently with a GUI of the client EHR.

\* \* \* \* \*